United States Patent [19]

Davis

[11] 4,307,716
[45] Dec. 29, 1981

[54] INVAGINATE SUPPORTED OVOID PESSARY

[76] Inventor: Alwyn K. Davis, 88 Pinecrest Rd., Thousand Oaks, Calif. 91360

[21] Appl. No.: 139,276

[22] Filed: Apr. 11, 1980

[51] Int. Cl.³ .............................................. A61F 5/46
[52] U.S. Cl. .................................................. 128/127
[58] Field of Search ............................... 128/127, 130

[56] References Cited

U.S. PATENT DOCUMENTS

| | | | |
|---|---|---|---|
| 1,164,275 | 12/1915 | Fleich | 128/127 |
| 2,452,229 | 10/1948 | DeBray et al. | 128/127 |
| 3,811,423 | 5/1974 | Dickinson et al. | 128/127 X |

Primary Examiner—John D. Yasko
Attorney, Agent, or Firm—William H. Maxwell

[57] ABSTRACT

An ovoid pessary for prevention of prolapse of the female organs through support thereof when inserted into the vaginal vault. Two elements are involved, one of body and the other a valve means, the latter having a set position for use whereby invaginate suction is effected by concavities on the body, and having a released position for withdrawal of the pessary without suction and providing means for manipulated removal. The two elements are made of soft pliable material and are readily disassembled for cleansing and re-use.

14 Claims, 5 Drawing Figures

INVAGINATE SUPPORTED OVOID PESSARY

BACKGROUND

This invention relates to a pessary for vaginal support against prolapse in situations where the deteriorating tonicity of the pelvic ligaments permits the descensus of the female organs. There are various degrees of descensus, a prolapse that permits severe intussusception being referred to as fourth degree and which can result in protusion of the cervix at the vulva. Although the pessary hereinafter disclosed is advantageously useable in lesser situations, it is particularly useful with persons who are not candidates for pelvic surgery, due to physical fitness and/or old age. In any case, the advent of such a problem within an individual is physiological and social as well as medical, and in those cases where surgery is not feasible, treatment with a pessary is often prescribed. It is the disorder of the internal female organs which is to be corrected, for example the displacement of the bladder that causes urinary incontenance and which is relieved by support with this pessary to effect a vesicular angle for proper functioning of the urethra and retention of urine.

Heretofore, pessaries for the purposes referred to herein have been difficult to insert and to remove, such devices being characterized by circular rings, elongated rings, inflated bladders, and cubes, cubes and/or solids wherein suction is afforded by the moist vaginal mucosa which invaginates into concavities are most annoying and even painful upon removal. It is a general object therefore to prevent annoyance and pain that would otherwise be caused by invaginate action which normally retains such devices in working position.

The vagina is that reproductive organ of the squamous mucus membrane canal that enters the pelvic cavity from the vulva, and into which the cervix of the uterus opens. The vagina is supported by and passes through the perineal sling, taking various positions in different individuals, but generally of tubular formation with the mucosa that invaginates and expansively folds together to form an elongated vault with the cervix normally protruding therein anteriorly at its innermost depth. The mucosa is readily expanded and will permit prolapse when the pelvic support weakens, and will permit the intrusion of cystourethroceles, rectoceles and the like. An object of this invention is to provide means which ensures invaginate retention of the pessary in use and which releases the suction thereof when the pessary is to be removed.

The perineal sling is that system of muscles which are normally toned to support the internal organs of the anatomy by means of an internal boarder or shoulder superior to the introitus and within the pelvic cavity and comprised of the following muscles with their facia and supporting structures; namely the pubococcygeus, levator ani, transverse perineal and bulbo-cavernosus muscles. It is this muscular boarder which forms the natural support upon which the device of the present invention rests. Accordingly, it is an object of this invention to provide a replaceable pessary that is releasably held in working position by the perineal sling.

An object of this invention is to improve pessarie of the type hereinabove referred to by including therein a valve means that releases the invaginate suction when removal is required. With the present invention, invaginate suction is normally maintained by said valve means during use, and by manipulation is released for facilitating removal without annoyance in breaking suction with the vaginal walls.

It is an object of this invention to provide a simple and sanitary unit of construction characterized by a single valve element that is adapted to be set in working position and that is shiftable to open suction concavities to atmosphere and to establish a pull stem for removal of the pessary. The valve means comprises a shiftable element in the form of an anchoring stem that has two positions, a set working position and a vent position engageable with the pessary body to withdraw the same from working position.

SUMMARY OF INVENTION

This is a pessary to be used in the support of female prolapse in the pelvic cavity and positioned for use in the vaginal vault. The pessary is comprised of two elements, the body with suction cavities and the valve means with a vent. The body is characteristically ovoid with its minor diameter occupied by concavities, and with the valve means extending through the body on its longitudinal axis. The valve means is inserted into the body from one end thereof and has limited stopped movement between two operable positions, one set position for use and the other a stopped position for vented withdrawal of the unit. The two elements are made of soft rubber or the like, the valve means is slideably sealed in the body and frictionally positioned therein, with provision for a draw string to facilitate removal by manipulation.

PREFERRED EMBODIMENT

Figure 1:
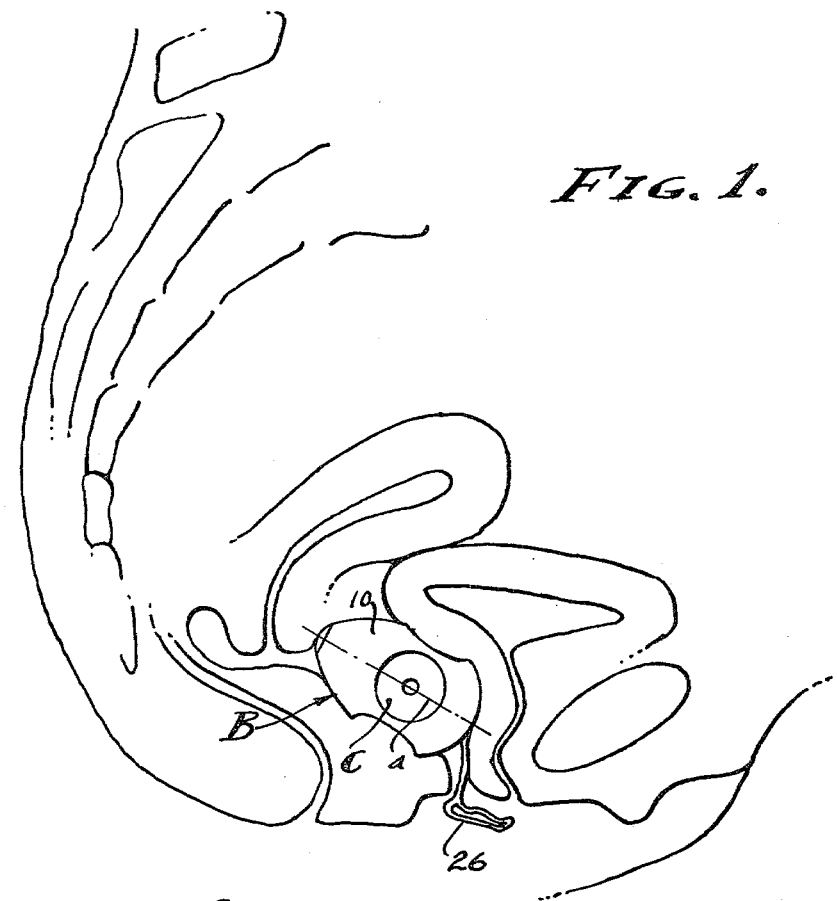
FIG. 1 is a cross sectional view taken through the central plane of the female anatomy, showing a typical installation of the invaginate supported ovoid pessary of the present invention.

Referring now to the drawings, the pessary herein disclosed is a two element device having two operable conditions, a normal use condition in which suction cavities are closed to atmosphere, and a released condition in which said cavities are open to atmosphere. As shown in FIG. 1 and the pessary is insertable into the vaginal vault in its ovoid form to be held in position by vaginate suction of the mucosa and by the surrounding perineal muscular boarder, thereby relating the pessary superior to the introitus normal for disposition of the cervix, uterus, and anterior - posterior vaginal walls toward a proper physiologic position. Simultaneously, occupancy of the pessary in the vaginal vault displaces rectocele hernias and the like, and re-establishes the normality of the urithro-vescular angle for retention of urine in the bladder. To such ends the pessary is employed as shown and comprised generally of an ovoid body B and a valve means V, assembled as a unit and inserted coaxially into the vaginal vault to substantially occupy the same. The body B is characteristically of oviform with concavities disposed peripherally about its diameter, and with the valve means V extending through the body on the longitudinal major axis a thereof. The elongation of the oviform can vary and is preferably substantially as shown with the valve-means V exposed at opposite terminal ends of said body.

The ovoid body B is an oviform of rubber or elastomeric material that presents a soft non-injurious and deformable structure. As shown, the ovoid is of eliptical longitudinal cross section and of circular transverse cross section, thereby establishing a diameter at its major transverse cross section and which is disposed concentrically about the longitudinal axis a. The invaginate suction for securement of the ovoid body in working position is achieved by providing one or more and preferably a circumferential series of concavities C. The concavities are alike and proportioned for most efficient invaginate retention. Accordingly, the concavities C are disposed on individual axes that are normal to and extend radially from the longitudinal axis a. In practice, the concavities are cone-shaped depressions with their vertexes or vertices at or near the axis a, and with their open bases adjoining the outer ovoid surface 10 of the body B. The four concavities engage with the natural folds of the vaginal mucosa posteriorly, anteriorly and laterally respectively.

In accordance with this invention, the body B is provided with a bore 11 opening coextensively therethrough along the axis a. The bore 11 individually truncates the vertex of each concavity C, so that each concavity opens into said bore. The bore 11 is cylindrical and preferably of uniform diameter throughout its length, opening at the forward end of the body for exposure to atmosphere. For cooperation with the valve means V next to be described, the rear end of the body B has a counterbore 12 of considerably larger diameter than the bore 11 and preferably with an internal groove 13 of limited radial extent, where it adjoins the body surface 10. The counterbore 12 is of a longitudinal extent to permit operational travel of the valve-means V, and it presents a shoulder 14 to positionably stop the valve means.

Figure 2:
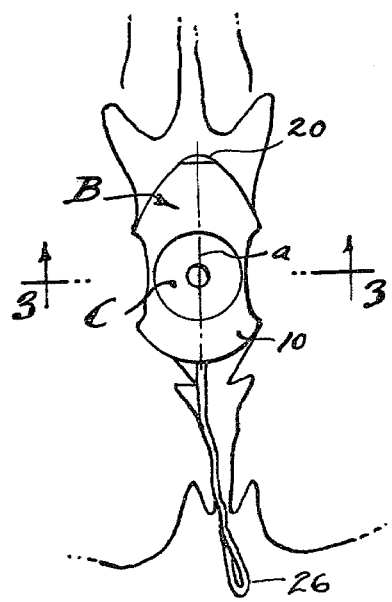
FIG. 2 is a transverse section of the said female anatomy.
Figure 3:
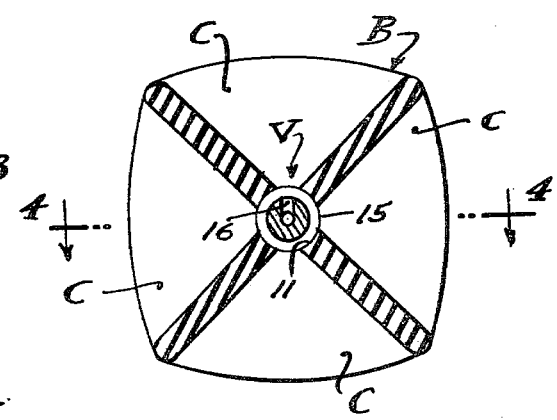
FIG. 3 is an enlarged sectional view of the pessary and taken as indicated by line 3—3 in FIG. 2.

The valve means C is a substantially rigid stem 15 of a material adapted to frictionally slide in the bore 11. To this end a plastic material can be employed, or the same material as that of the body B. However, a more rigid material is contemplated for the valve-means C, inasmuch as it is protectively housed within the bore 11 and requires structural strength for its operational functions. Accordingly, the stem 15 is of a diameter to positionably press into the bore 11 and is of a length coextensive with the body B. The stem has a port 16 normally rearward of the concavities C opening into the bore 11, and a passage 17 extending forwardly from the port and opening to atmosphere at the forward end of the stem. In other words, the stem 15 is tubular as it extends forwardly from the port 16, the port 16 being forwardly offset from the concavity openings into the bore 11. In practice, the port communication with all cavities is assured by a port or ports encompassed by a channel 18 of limited radial extent. Normal positioning of the stem 15 is assured when it is coextensively positioned in body B as shown in FIGS. 1, 2 and 5.

In accordance with this invention, the valve positioning feature for release and removal of the pessary is provided for in the head 20 at the rear end of the stem 15. As shown, the head 20 slides through counterbore 12 and has a peripheral rib 21 (see FIG. 4) that snaps into the groove 13 to ensure working position. The forward face 22 of the head is normally spaced from shoulder 14 and is engageable therewith when the port or ports 16 are in alignment with the truncated openings of the concavities into the bore 11. Operation of the stem 15 is facilitated by a loop 25 at the forward end of the stem and from which a lanyard 26 extends, leaving the passage 17 open to atmosphere.

A feature is the venting of the innermost end of the body B through the head 20, there being a port 16' separated from port 16 by a flange, and a passage 17' extending rearwardly and opening through the head 20. The port 16' is encompassed by a channel 18' and the channels 18 and 18' are proportioned to be simultaneously opened into the concavities C when valve means V is positioned as shown in FIG. 5. However, when valve means V is positioned as in FIGS. 1-4 the ports 16 and 16' are closed through engagement of stem 15 in the bore 11, thereby sealing off the concavities C and head 20.

Figure 4:
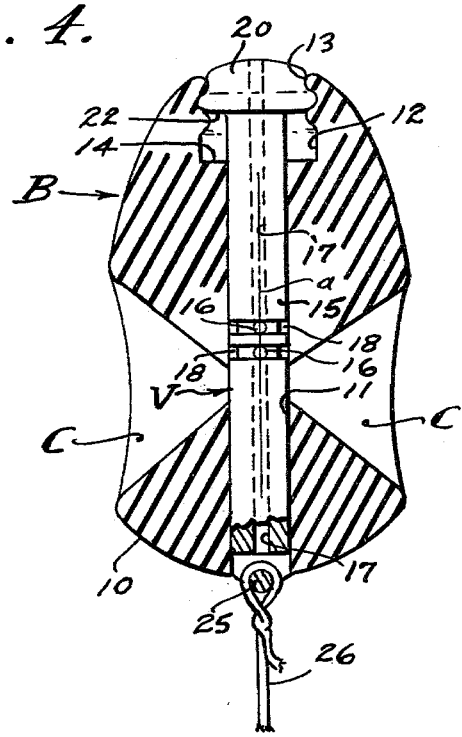
FIG. 4 is a transverse sectional view taken as indicated by line 4—4 on FIG. 3.
Figure 5:
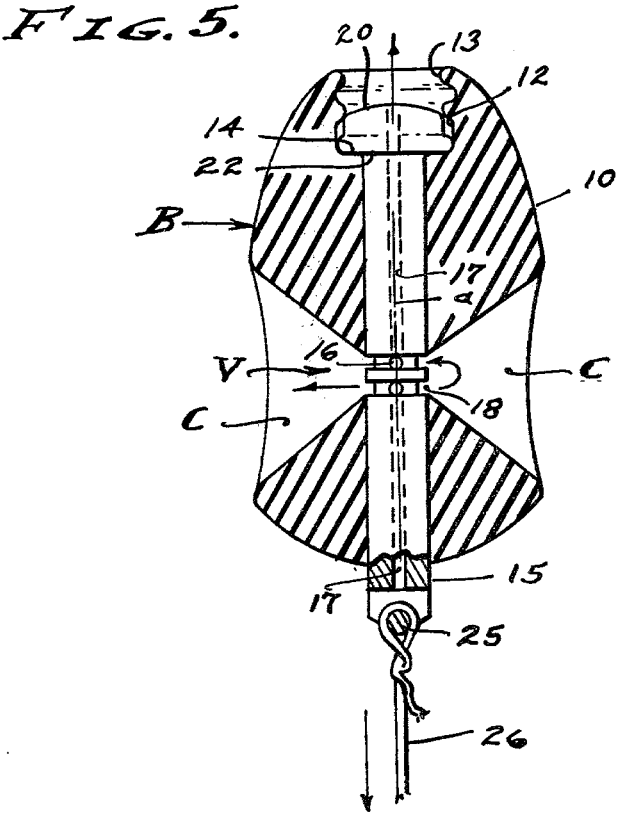
FIG. 5 is a view similar to FIG. 4 showing the pessary in its withdrawal condition and vented to atmosphere.

From the foregoing it will be seen that the concavities C of the body B are closed by the valve-means V positioned coextensively within body B as shown in FIG. 4, and alternately opened to atmosphere by shifting the stem 15 to the stopped position shown in FIG. 5. With proper design and selection of material for a suitable coefficient of friction between the elements B and V, a working or release position can be maintained. However, a working positioning is assured with a detent action by providing the groove 13 and rib 21. Complete disassembly is achieved by withdrawing the stem 15 rearwardly, thereby exposing all working surfaces for cleaning. Re-assembly is then an easy matter, there being but one mode in which the two elements can be refitted together, the body B of softer material complying frictionally onto the reinforcing stem of structurally harder material. Insertion and withdrawal is accomplished with facility due to the ovoid shape of firm yet compressible body that can be manipulated to dilate the introitus and moved therethrough.

Having described only a typical preferred form and application of my invention, I do not wish to be limited or restricted to the specific details herein set forth, but wish to reserve to myself any modifications or variations that may appear to those skilled in the art as set forth within the limits of the following claims.

I claim:
1. An invaginate supported pessary for the prevention of prolapse of the female organs and adapted to rest upon the internal boarder of the perineal sling, and including;
   an ovoid body having a bore therethrough on its major axis, and a least one concavity open laterally from the bore to an outer ovoid surface of the body,
   and valve means shiftable in said bore between a position closing the at least one concavity to the bore and a position opening the at least one concavity into the bore and vented at one end of the body.
2. The invaginate supported pessary as set forth in claim 1, wherein the ovoid body is made of a soft non-injurious material.
3. The invaginate supported pessary as set forth in claim 1, wherein the ovoid body is made of a soft non-injurious and firm-compressible material for ease of insertion and removal through the introitus.

4. The invaginate supported pessary as set forth in claim 1, wherein the valve means comprises a stem slidable in the bore through the body.

5. The invaginate supported pessary as set forth in claim 1, wherein the ovoid body is made of a firm-compressible non-injurious material, and wherein a stem of harder reinforcing material is slideable in the bore through the body.

6. The invaginate supported pessary as set forth in claim 1, wherein the valve means comprises a stem opening at atmosphere at the lower end of the ovoid body.

7. The invaginate supported pessary as set forth in claim 1, wherein the valve means comprises a stem opening at and having a lanyard extending from the lower end of the ovoid body.

8. The invaginate supported pessary as set forth in claim 1, wherein the valve means comprises a stem with a lateral port normally closed by engagement within the bore through the body and opened by alignment thereof with said at least one concavity open from said bore and in communication with atmosphere via a passage through the stem and opening at said one end of the body.

9. The invaginate supported pessary as set forth in claim 1, wherein the valve means comprises a head with restricted movement into a counterbore in the upper end of the ovoid body.

10. The invaginate supported pessary as set forth in claim 1, wherein the valve means comprises a head with restricted detented movement into a counterbore in the upper end of the ovoid body.

11. The invaginate supported pessary as set forth in claim 1, wherein the valve means comprises a stem having separate passages opening at the lower and upper ends of the ovoid body, there being lateral ports in the stem and separated by a flange on the stem normally engaged within the bore through the body to close said ports, and opened by alignment thereof with said at least one concavity open from said bore to atmosphere at the lower said one end of the body.

12. The invaginate supported pessary as set forth in claim 1, wherein the valve means comprises a stem having a head with restricted movement into a counterbore in the upper end of the body and having separate passages opening at the lower and upper ends of the ovoid body, there being lateral ports in the stem and separated by a flange on the stem normally engaged within the bore through the body to close said ports, and opened by alignment thereof with said at least one concavity open from said bore to atmosphere at the lower said one end of the body.

13. The invaginate supported pessary as set forth in any one of claims 1–12, wherein a plurality of concavities are disposed in a circumferential plane normal to the major axis of the ovoid body.

14. The invaginate supported pessary as set forth in any one of claims 1–12, wherein a plurality of four right angularly related concavities are disposed in a circumferential plane normal to the major axis of the ovoid body for their invaginate suction engagement with the natural folds of the vaginal mucosa posteriorly, anteriorly and laterally respectively.

* * * * *